United States Patent [19]

Klein et al.

[11] Patent Number: 5,221,033
[45] Date of Patent: Jun. 22, 1993

[54] METHOD AND APPARATUS FOR ANTI-CONTAMINATION DISPENSING OF CUT-SEPARABLE MEDICAL DEVICES

[76] Inventors: Douglas J. Klein, 17681 Crestline Dr.; Paul E. Klein, 928 Lake Shore Rd., both of Lake Oswego, Oreg. 97034

[21] Appl. No.: 883,894

[22] Filed: May 12, 1992

Related U.S. Application Data

[63] Continuation of Ser. No. 628,614, Dec. 17, 1990, abandoned.

[51] Int. Cl.5 ............................................. B26F 3/02
[52] U.S. Cl. ...................................... 225/52; 225/39; 225/56; 206/63.5
[58] Field of Search ...................... 225/4, 5, 16, 39, 46, 225/52, 56, 77; 206/390, 440, 63.5, 409; 221/33, 63

[56] References Cited

U.S. PATENT DOCUMENTS

| | | | |
|---|---|---|---|
| 1,869,729 | 8/1932 | Zuckerman | 225/56 X |
| 2,701,692 | 2/1955 | Guyer | 225/56 X |
| 2,878,928 | 3/1959 | Ivy | 225/56 |
| 3,239,117 | 3/1966 | Letchworth | 225/39 X |
| 3,246,814 | 4/1966 | Lovell et al. | 225/52 X |
| 3,903,601 | 9/1975 | Anderson et al. | 433/18 X |
| 4,436,510 | 3/1984 | Klein | 433/4 |
| 4,756,460 | 7/1988 | Ornros | 225/54 |
| 5,054,647 | 10/1991 | Yawata | 221/63 X |

*Primary Examiner*—Eugenia Jones
*Attorney, Agent, or Firm*—Kolisch, Hartwell, Dickinson, McCormack & Heuser

[57] ABSTRACT

A dispenser/separator for contamination-free dispensing of a supply of cut-separable medical devices is disclosed which includes anti-contamination structure for enclosing the supply. The anti-contamination structure includes an exit port for allowing the supply to be pulled therethrough in a first direction to expose a device. Also disclosed is a cutter for separating such an exposed device from the supply by pulling the supply against the cutter in a second direction that is at an oblique angle relative to the first direction. In the preferred embodiment, the exit port takes the form of a resistance control aperture, and the cutter takes the form of a stationary knife blade that is positioned adjacent the aperture.

3 Claims, 1 Drawing Sheet

METHOD AND APPARATUS FOR ANTI-CONTAMINATION DISPENSING OF CUT-SEPARABLE MEDICAL DEVICES

This is a continuation of application Ser. No. 07/628,614 filed Dec. 17, 1990 and now abandoned.

BACKGROUND OF THE INVENTION

The present invention relates to a method and apparatus for dispensing/separating medical devices, and more particularly to a novel dispenser/separator system for contamination-free dispensing of a supply of cut-separable medical devices. A preferred embodiment and practice of the invention are disclosed in the setting of handling orthodontic tools.

To prevent the spread of communicable diseases, particularly AIDS, there is an ever-increasing need to establish anti-contamination protocol for delivery of various types of medical and dental services by health care professionals. For example, there is a need for orthodontists to follow anti-contamination protocol when dispensing intraoral tools to perform ligature operations. When performing such an operation, it is known that orthodontists use cut-separable intraoral tools such as those disclosed in U.S. Pat. Nos. 3,530,583 to Klein et al., 3,903,601 to Anderson et al. and 4,436,510 to Klein.

Totally lacking in conventional methods and apparatus for anti-contamination dispensing of such tools is a way of preventing cross-contamination. Cross-contamination can occur when orthodontists repeatedly dispense such tools from their respective packages.

To understand what is meant by cross-contamination, one must first understand conventional packaging systems. Such systems are not designed for controlled dispensing of such tools, which, as noted above, are often formed in chain-like or other multiple-unit-like structures with cut-separable tools.

In other words, once an orthodontist opens a conventional package all the tools in the package are exposed. Then, as is common, the orthodontist will take a desired portion of the tools by separating it from the full supply. With the desired portion, the orthodontist begins work in a patient's mouth where he or she will have gloved-hand contact with the patient's blood and saliva, i.e. the orthodontist's gloved hands will become contaminated.

Cross-contamination is likely to occur when the orthodontist returns to the opened package for additional tools. At this point, the orthodontist will use his or her contaminated gloved hands to separate another portion of the tools from the chain. In addition, the orthodontist's gloved hands may contact portions of the chain which will not be needed for the patient. Such contaminated tools will of course need to be disposed of or sterilized.

It is therefore an object of the present invention to provide a method and apparatus for anti-contamination dispensing/separating of a supply of cut-separable medical devices.

Another object of the present invention is to provide such a method and apparatus that includes controlled dispensing of such devices.

A still further object of the present invention is to provide such a method and apparatus that does not require contact between a health care professional's gloved hand and portions of the supply not immediately needed for use.

Yet another object of the present invention is to provide such a method that is relatively fast.

SUMMARY OF THE INVENTION

The present invention achieves the above objects by providing apparatus that takes the form of a dispenser/separator system for contamination-free dispensing of a supply of cut-separable medical devices. The apparatus includes anti-contamination means for enclosing the supply, with the same defining an exit port for allowing the supply to be pulled therethrough in a first direction to expose a device. Also included is means for separating such an exposed device from the supply by pulling the supply against the separating means in a second direction that is at an oblique angle relative to the first direction.

In the preferred embodiment, the exit port takes the form of a resistance control aperture for controllably allowing such medical devices to be pulled therethrough. Also, the separating means includes a stationary knife blade.

The invention also embodies a method for contamination-free dispensing of an anti-contamination supply of cut-separable medical devices from an anti-contamination enclosure. Such method includes dispensing a portion of the supply from the enclosure in a first direction. The method also includes moving a desired portion of the supply against a cutter and pulling the portion of the supply that is outward of the cutter in a second direction, thus to separate such portion from the supply. The mentioned "second-direction" motion minimizes the possibility that the act of separating will cause additional still-to-be-dispensed articles to be pulled out of the protective environment of the enclosure.

These and additional objects and advantages of the present invention will be more readily understood after a consideration of the drawings and the detailed description of the preferred embodiment.

DETAILED DESCRIPTION OF THE PREFERRED EMBODIMENT

Figure 1:
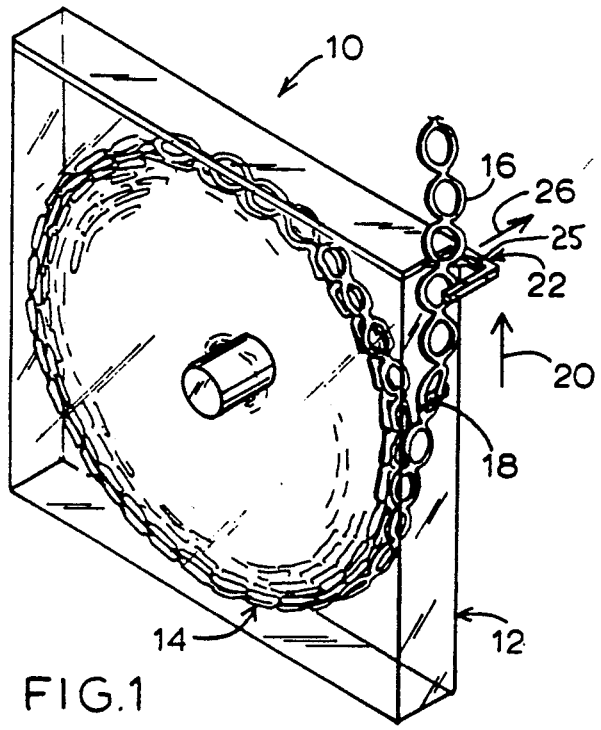
FIG. 1 is a perspective view of the apparatus of the present invention with a supply of cut-separable intraoral devices.

Turning now to the drawings, FIG. 1 shows generally at 10 the preferred embodiment of the dispenser/separator system of the present invention. System 10, which for reasons soon to be explained may also be thought of as a differentiated-motion, anti-contamination system, includes anti-contamination means 12 for enclosing a supply 14 of cut-separable repeating intraoral tools 16. In the system now being described, tools 16 are elastomeric O-rings joined in a long chain.

While system 10 is described herein with a supply of intraoral tools, it should be understood that any type of cut-separable spoolable medical device could be used. Also, means 12 may take the form of a housing or enclosure.

It should be understood that housing 12 may be suitably structured using conventional methods so that it is free standing. Alternatively, housing 12 could be structured to attach to separate stand structure as is more particularly described in our copending application, Ser. No. 07/359,988, filed May 31, 1989 and entitled "Anti-Contamination Orthodontic Device Dispenser".

Figure 2:
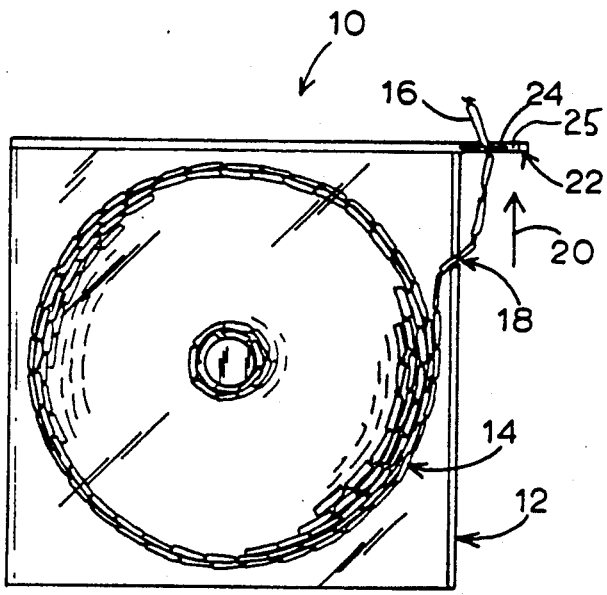
FIG. 2 is a side-elevational view of the apparatus of FIG. 1.
Figure 4:
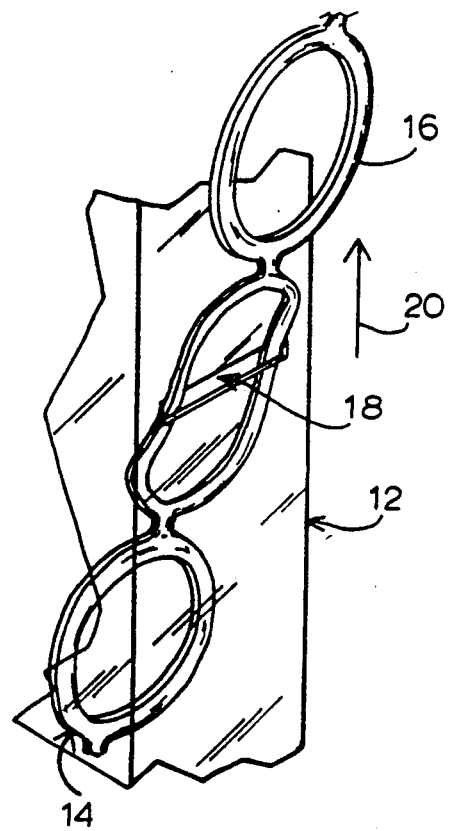
FIG. 4 is a fragmentary, enlarged perspective view of another portion of the apparatus of FIG. 1.

Continuing with the description of FIG. 1, and also referring for a moment to FIGS. 2 and 4 as well, housing 12 is structured to define an exit port 18 for allowing supply 14 to be pulled therethrough in a first direction along a first motion axis, represented by arrow 20. Port 18, which may also be thought of as a dispensing port, is formed as a resistance-control aperture, or slot, in housing 12 for controllably allowing tools 16 to be pulled therethrough, i.e., slot 18 is sized to require slight deformation of each separating tool 16 in order for the latter to pass through the slot. The resistance-control aperture can take a form other than a slot.

Referring back to FIG. 1, system 10 also includes means 22 for separating tool(s) 16 that are exposed after a desired portion of supply 14 is pulled through port 18. Means 22, also referred to herein as a cutter, is connected to housing 12 and positioned adjacent port or aperture 18. A stationary knife blade 24 is included in cutter 22.

Cutter 22 also includes an examination section 25 which allows the chain of tools 16 to be examined before moving the chain against blade 24 to perform a to-be-described cutting operation.

Figure 3:
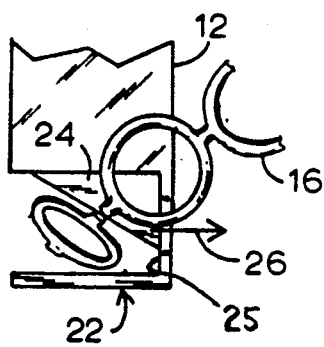
FIG. 3 is a fragmentary, slightly enlarged top view of a portion of the apparatus of FIG. 1.

Referring to FIGS. 1 and 3, cutter 22 is positioned relative to housing 12 so that a desired portion of supply 14 can be moved in a second, separating direction along a second motion axis shown by arrow 26. The second direction is different from the first direction and is at an oblique angle relative to the same. As an important consequence, the act of separating can be accomplished without simultaneously pulling additional tools from the protected environment within the enclosure.

Operation

To use system 10 in practice of the method of the present invention, an orthodontist dispenses a desired portion of supply 14 from housing 12 in the first direction shown by arrow 20. While undepicted, the orthodontist may use any conventional way to dispense supply 14. That is, for example, he or she may use a hemostat. Also, it should be noted that examination section 25 provides a convenient place for the supply to rest while the orthodontist chooses the desired portion.

Next, referring to FIGS. 1 and 3, the orthodontist moves the desired portion against cutter 22, and pulls the same in the second direction shown by arrow 26, thus to separate the desired portion from the supply.

Such movement of the supply in the second direction (arrow 26) along the second motion axis has, as has been mentioned, no substantial effect on movement of supply 14 relative to the first direction (arrow 20) along the first motion axis. In addition, referring to FIG. 4, port 18 will allow for controlled dispensing in the first direction because it is, as described earlier, a resistance-control aperture that is structured somewhat smaller than each tool 16 so that the tool must deform somewhat to pass therethrough.

Thus, it should be clear that the method and apparatus of the present invention provide for controlled, relatively fast, anti-contamination dispensing/separating of supply 14 of cut-separable intraoral units 16. Using system 10, an orthodontist does not cross-contaminate non-dispensed tools because the system can be used without there being any contact with portions of the supply not immediately needed for use.

While the present invention has been shown and described with reference to the foregoing preferred embodiment and practice method, it will be apparent to those skilled in the art that other changes in form and detail may be made therein without departing from the spirit and scope of the invention as defined in the appended claims.

What is claimed is:

1. A differentiated-motion, anti-contamination dispenser and separator system for dispensing intraoral tools comprising:
   a spooled supply of repeating, cut-separable elastomeric intraoral tools;
   an anti-contamination housing for enclosing said supply, said housing including a fixed-configuration dispensing port in the form of a resistance-control aperture for allowing said supply to be pulled deformably therethrough, without deformation of the port, in a first direction which is generally tangential relative to the spooled tools; and
   a cutter positioned adjacent said housing for separating a desired intraoral tool from said supply by moving a desired portion of said supply against said cutter in a second direction at an oblique angle relative to the first direction, with the movement in the second direction having no substantial effect on movement of said supply in the first direction.

2. The system of claim 1, wherein said cutter is connected to said housing and positioned adjacent said aperture.

3. The system of claim 2, wherein said cutter is a stationary knife blade.

* * * * *